United States Patent [19]

Gibson et al.

[11] Patent Number: 5,001,239
[45] Date of Patent: Mar. 19, 1991

[54] FORMATION OF REISSERT COMPOUND OF BENZOYL BENZIMIDAZOLE

[75] Inventors: Harry W. Gibson; Yajnanarayana H. R. Jois, both of Blacksburg, Va.

[73] Assignee: Virginia Tech Intellectual Properties, Inc., Blacksburg, Va.

[21] Appl. No.: 418,360

[22] Filed: Oct. 6, 1989

[51] Int. Cl.$^5$ ............................................ C07D 235/16
[52] U.S. Cl. .................................................... 548/331
[58] Field of Search ........................................ 548/331

[56] References Cited

PUBLICATIONS

Uff et al., J. Chem. Research (S), Issue 12 (Dec. 1989), pp. 386–387.
Katritzky, Comprehensive Heterocyclic Chemistry, vol. 2, 1984, pp. 248–255.
Uff et al., J. Chem. Soc., Chem. Commun., 1984, pp. 1245–1246.
Popp, Frank D., Heterocycles, 1980, vol. 14, No. 7, pp. 1033–1043.
Uff et al., J. Heterocyclic Chem., 1987, vol. 24, pp. 1349–1351.
Popp, Frank D., Adv. in Heterocyclic Chemistry, 1968, vol. 9, p. 2.

Primary Examiner—Mukund J. Shah
Assistant Examiner—Philip I. Dalton
Attorney, Agent, or Firm—Richard P. Fennelly; Louis A. Morris

[57] ABSTRACT

The Reissert compound of 1-benzoylbenzimidazole can be formed by reaction of an acid chloride (e.g., benzoyl chloride) and cyanide (e.g., trimethylsilyl cyanide) with benzoyl benzimidazole. It has the formula:

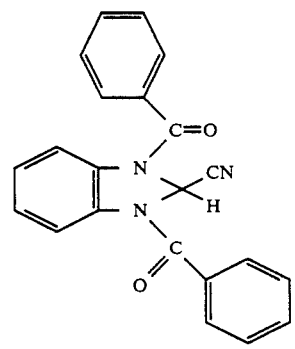

and is useful as an intermediate in organic synthesis.

1 Claim, 1 Drawing Sheet

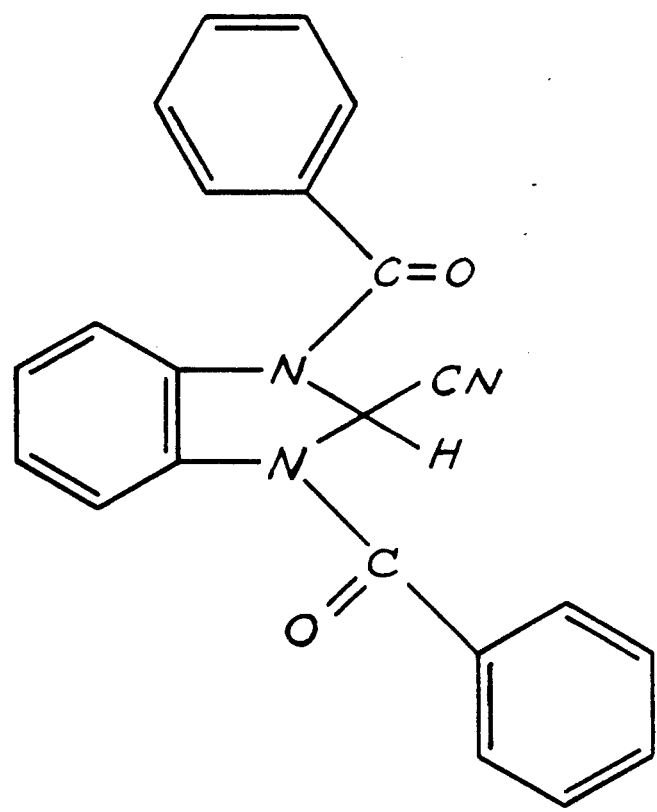

FORMATION OF REISSERT COMPOUND OF BENZOYL BENZIMIDAZOLE

BACKGROUND OF THE INVENTION

The benzimidazole nucleus forms the basis of a number of useful materials, including polymeric structural materials (fibers) and biologically active compounds. Thus, ways of elaborating the molecular structure, particularly the 2-position, are needed in many applications.

In theory, Reissert compounds derived from benzimidazole offer the opportunity for such chemical manipulations (see Advances in Heterocyclic Chemistry, 1979, 24 187-214 for a review). Although analogs derived from chloroformates have been reported (see J. Heterocyclic Chem., 1987, 24, 1349-1351), all attempts to produce the more synthetically useful Reissert compounds by reaction of benzimidazole with acid chlorides in the presence of a cyanide source led to destruction of the benzimidazole ring system (see J. Chem. Soc., Chem. Comm., 1984, 1245-1246).

The instant invention is a method for the synthesis of Reissert compounds from benzimidazole by a two-step procedure.

DESCRIPTION OF THE INVENTION

The present invention relates to the formation of the Reissert compounds of 1-benzoylbenzimidazole.

The first step in the process involves the formation of 1-benzoylbenzimidazole by reaction of benzoyl chloride and benzimidazole in a suitable organic solvent (e.g., dimethylformamide) in the presence of base (e.g., triethylamine).

The thus formed 1-benzoylbenzimidazole is then subjected to a Reissert reaction using an acid chloride, e.g., benzoyl chloride and cyanide source (e.g., trimethylsilyl cyanide) using N-methylpyrrolidone as a solvent. The Reissert compound has the formula shown in FIG. 1 and has utility as an intermediate in organic synthesis.

The instant invention is illustrated by the Examples which follow.

EXAMPLE 1

To a well stirring solution of 1-benzoylbenzimidazole (0.0025 mole, 0.56 gm) in N-methylpyrrolidone (5 ml) was added benzoyl chloride (0.0025 mole, 0.35 gm) and trimethylsilyl cyanide (0.00257 mole, 0.273 gm). The reaction mixture was stirred for five days and was quenched by pouring into water. This solution was extracted with dichloromethane (3×75 ml). The organic layer was washed with 8% HCl (3×50 ml), aqueous saturated bicarbonate (3×50 ml), water (3×50 ml) and was dried. The crude yield was 600 mg (67.5%). A purified product was obtained by treating the crude product once with activated carbon (NORIT brand) and crystallizing the product (2-cyano-1,3-dibenzoyl-2,3-dihydro benzimidazole) with ethyl acetate and hexane.

Melting point: 193°-194° C.

Analysis: Theory: C 74.77%, H 4.28%, and N 11.89%. Found: C 74.64%, H 4.33%, and N 11.83%.

$^1$H NMR (DNSO—d$_6$): 7.75-7.55 (m, 10H COC$_6$H$_5$), 6.99 (s, 1H, C$_2$—H), 6.98-6.85 (m, 2H, C$_3$—H and C$_6$—H), 6.7-6.3 (s,2H, C$_4$—H and C$_7$—H).

We claim:

1. A Reissert compound of the formula followed by a depiction of the formula from the Figure as follows:

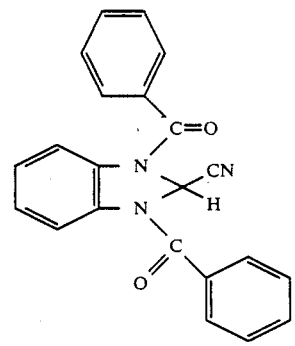

UNITED STATES PATENT AND TRADEMARK OFFICE
CERTIFICATE OF CORRECTION

PATENT NO. : 5,001,239
DATED : March 19, 1991
INVENTOR(S) : Harry W. Gibson - Yajnanarayana H. R. Jois It is certified that error appears in the above-identified patent and that said Letters Patent is hereby corrected as shown below: Column 2, Claim 1, lines 1-2, delete "followed by a depiction of the formula from the Figure as follows".

Signed and Sealed this

Twenty-sixth Day of October, 1993

Attest:

BRUCE LEHMAN

*Attesting Officer*         *Commissioner of Patents and Trademarks*